United States Patent [19]
Morrow et al.

[11] Patent Number: 5,149,835
[45] Date of Patent: Sep. 22, 1992

[54] SUBSTITUTED MEVALONOLACTONES, AND METHODS FOR STEREOSELECTIVE PREPARATION THEREOF AND DESMETHYL HOMOLOGUES THEREOF

[75] Inventors: Cary J. Morrow; Joseph M. Eridon, both of Albuquerque, N. Mex.

[73] Assignee: University of New Mexico, Albuquerque, N. Mex.

[21] Appl. No.: 343,772

[22] Filed: Apr. 27, 1989

[51] Int. Cl.$^5$ .......................................... C07D 309/30
[52] U.S. Cl. .................................................. 549/292
[58] Field of Search ........................................ 549/292

[56] References Cited

U.S. PATENT DOCUMENTS

| | | | |
|---|---|---|---|
| 2,420,250 | 5/1947 | Kyrides et al. | 260/344 |
| 2,569,064 | 9/1951 | Ladd et al. | 260/344 |
| 2,968,568 | 1/1961 | Preuss | 99/129 |
| 3,119,824 | 1/1964 | Hulcher et al. | 549/292 |
| 3,346,594 | 10/1967 | Rahllay et al. | 260/343 |
| 3,992,417 | 11/1976 | Dessau et al. | 260/343.6 |
| 4,175,089 | 11/1979 | Heiba et al. | 260/343.6 |
| 4,309,352 | 1/1982 | Ho | 260/343.5 |
| 4,348,535 | 9/1982 | Schmidt | 560/124 |
| 4,499,289 | 2/1985 | Baran et al. | 549/292 |
| 4,513,005 | 4/1985 | Baker et al. | 549/292 |
| 4,622,338 | 11/1986 | Baran et al. | 549/292 |

OTHER PUBLICATIONS

Bongini et al., "Regio- and Stereocontrolled Synthesis of Epoxy Alcohols and Triols from Allylic and Homoallylic Alcohols via Iodo Carbonates", *J. Org. Chem.*, 1982, 47, 4626-4633.

Hirama et al., "Chiral Total Synthesis of Compactin", *J. Am. Chem. Soc.*, 1982, 104, 4251-4253.

Danishefshy et al., "Lewis Acid Catalyzed Cyclocondensations of Functionalized Dienes with Aldehydes", *J. Am. Chem. Soc.*, 1982, 104, 358-360.

Raymond L. Funk et al., "Hypocholesterolemic Agent Compactin (ML-236B) Total Synthesis of the Hexahydronaphthalene Portion", *J. Org. Chem.*, 1982, 47, 180-182.

Ethan A. Deutsch, "Synthesis of the Hexahydronaphthalene Moiety of (±)-Compactin (ML-236B)", *J. Org. Chem.*, 1982, 47, 2682-2684.

Prugh et al., "Methyl 3-O-Benzyl-2,4,6-Trideoxy-6-Iodo-a-D-Erythro-Hexopyranoside, A Chiral Synthon for the Synthesis of Inhibitors of HMG-CoA Reductase", *Tetrahedron Letters*, vol. 23, No. 3, pp. 281-284, 1982.

Ta-Jyh Lee et al., "Structural Modification of Mevinolin", *J. Org. Chem.*, 1982, 47, 4750-4757.

Anderson et al., "Synthetic Studies Related to Compactin and Mevinolin: A New Synthesis of the Hexahydronaphthalene Portion of Compactin", *Tetrahedron Letters*, vol. 24, No. 13, 1373-1376, 1983.

Kuo et al., "Reductive Transformation and Cyclopropanation of Mevinolin (6a-Methylcompactin), Generation of Chirality in the 1,4-Hydrostannation of a Cyclic Diene", *J. Org. Chem.*, 1983, 48, 1991-1998.

Deutsch et al., "Synthesis of the Hexahydronaphthalene Moiety of (±)-Mevinolin", *Tetrahedron Letters*, vol. 24, No. 35, pp. 3701-3704, 1983.

Funk et al., "Hypocholesterolemic Agent Compactin. An Alternative Diels-Alder Strategy for the Synthesis of the Hexahydronaphthalene Portion", *Tetrahedron Letters*, vol. 25, No. 16, 1655-1658, 1984.

Majewski et al., "Synthetic Studies Related to Compactin and Mevinolin: A New Synthesis of the Lactone System", *Tetrahedron Letters*, vol. 25, No. 20, pp. 2101-2104, 1984.

Prasad et al., "A Novel Diasterioselective Synthesis of the Lactone Moiety of Compactin", *Tetrahedron Letters*, vol. 25, No. 23, pp. 2435-2438 (1984).

Rosen et al., "Synthetic and Biological Studies of Compactin and Related Compounds. 2. Synthesis of the Lactone Moiety of Compactin", *J. Org. Chem.*, 1984, 49, 3994-4003.

Wang et al., "Total Synthesis of (±)-Compactin (ML-236B)", *J. Am. Chem. Soc.*, 1981, 103, 6538-6539.

Yang et al., "Mevinic Acids and Analogues: Preparation of a Key Chiral Intermediate", *Tetrahedron Letters*, vol. 23, No. 42, pp. 4305-4308, 1982.

Yang et al., "Total Synthesis of (±)-Dihydrocompactin", *J. Am. Chem. Soc.*, 1984, 106, 3811-3814.

Falck et al., "Total Synthesis of (±)-Dihydromevinolin", *Tetrahedron Letters*, vol. 25, No. 33, pp. 3563-3566, 1984.

G. C. Fisher et al., *J. Org. Chem.*, "Irreducible Analogues of Mevaldic Acid Coenzyme A Hemithioacetal...", 50 (12), pp. 2011-2019, (1985).

R. Tschesche, et al., *Justus Liebigs Annelen Der. Chemie*, "Syntheson von Substiturerten B-hydroxy-B-methyl--glutersainen...", 631, 61-76, (1960).

P. A. Bartlett, et al., *J. Am. Chem. Soc.*, 100 (12), "Stereoselective epoxidation of acyclic olefinic carboxylic acids via iodolactonization", pp. 3950-3952 (1978).

*Primary Examiner*—Glennon H. Hollrah
*Assistant Examiner*—Mark W. Russell
*Attorney, Agent, or Firm*—Lowe, Price, LeBlanc & Becker

[57] ABSTRACT

Novel 3-hydroxyl, 5-halo derivatized mevalonolactones and a stereospecific method of preparing a transsubstituted mevalonolactone.

A stereospecific method of preparing a 3-hydroxyl 5-trans mevalonolactone of the formula

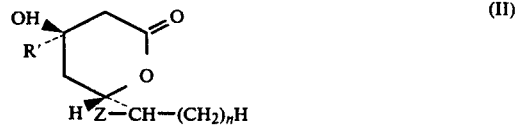

(II)

wherein n is 0-12, R' is $CH_3(CH_2)_m$, wherein m is 0-8, and Z is as defined in the specification.

7 Claims, No Drawings

SUBSTITUTED MEVALONOLACTONES, AND METHODS FOR STEREOSELECTIVE PREPARATION THEREOF AND DESMETHYL HOMOLOGUES THEREOF

BACKGROUND OF THE INVENTION

1. Field of the Invention This invention relates to novel C5-trans-substituted haloalkyl mevalonolactones and desmethyl homologues thereof. This invention also relates to a novel method for preparing 5-trans-substituted mevalonolactones which are useful as intermediates in the synthesis of biologically active derivatives evidencing, e.g., hypocholesteremic activities. This invention in addition relates to a method for preparing such hypocholesteremic derivatives.

2. Description of the Background

Many synthetic routes for preparing mevalonolactone derivatives have been developed, most of them yielding stereoisomeric mixtures of the 3,5-dyhydroxy moiety of the mevalonolactone system.

The two stereo isomers are referred to as either cis/-trans or threo/erythro depending upon whether the compounds are in the lactone (cyclic) or open chain form which are depicted in Scheme III hereinbelow.

Only one of the isomers in these mixtures usually shows significant biological activity. This is generally the trans lactone isomer which corresponds to the erythro isomer of the open chain system. The general synthetic methods known for the preparation of gamma and delta butyrolactones produce mixtures of the two stereoisomers. Non chiral mixtures of gamma or delta aliphatic lactones have been prepared by a variety of methods (see, U.S. Pat. Nos. 2,420,250; 3,992,417; 4,175,089; 2,569,064; 2,968,568; 4,309,352; 3,346,594; 4,499,289; 4,348,535; 4,513,005 and 4,622,338, among others)

Newer synthetic schemes to obtain derivatized lactones other than the six-member ring lactone disclosed herein seem to favor the trans isomer over the cis isomer However, none of the known processes results in a trans isomer substantially free of the cis isomer (see, Gonzalez and Bartlett, "Stereocontrolled Iodolactonization of Acyclic Olefinic Acids: The trans and cis isomers of 4,5-dihydro-5-iodomethyl-4-phenyl-2(3H)-furanone", Organic Synthesis 64: 175 (1985); A. Bongini, G. Cardillo, M. Orena, G. Porzi, and S Sandri, "Regio- and Stereo-controlled Synthesis of Epoxy Alcohols and Triols from Allylic and Homoallylic Alcohols via Iodo Carbonates", J. Org. Chem 1982, 47, 4626–4633; Wang et al, J. Amer. Chem Soc 103:6538 (1981); Hirama et al, Ibid 104: 4251 (1982); Grieco et al, Ibid. 105:1403 (1983); Girotra et al, Tetrahedron Lett. 23:5501 (1982); Girotra et al, Ibid. 24:3687 (1983); Hirama et al, Tetrahedron Lett 24:1811 (1983); Danishefsky et al, J. Amer Chem. Soc. 104:358 (1982); Funk et al, J. Org. Chem. 47:180 (1982); Deutsch et al, Ibid. 47:2682 (1982); Prugh et al, Tetrahedron Lett. 23:281 (1982); Wang et al, Ibid. 23:4305 (1982); Heathcock et al, Ibid. 23:4747 (1982); Lee et al, J. Org. Chem 47:4750 (1982); Anderson et al, Tetrahedron Lett. 24:1373 (1983); Kuo et al, J. Org. Chem 48:1991 (1983); Deutsch et al, Tetrahedron Lett 24:3701 (1983); Funk et al, Ibid 25:1655 (1984); Majeweski et al, Ibid. 25:2101 (1984); Prasad et al, Ibid. 25:2435 (1984); Rosen et al, J. Org. Chem. 49:3994 (1984); Wang et al, J. Amer. Chem Soc. 106 3811 (1984); Falck et al, Tetrahedron Lett 25:3563 (1984); and Funk et al, J. Amer. Chem. Soc. (1985), U.S. Pat. No. 4,503,072 to Hoffman et al; U.S. Pat. No. 4,582,915 to Sleteinger et al and U.S. Pat. No. 4,342,767 to Albers-Schonberg et al, among others). Some of these methods are totally synthetic while others rely on an initial fermentation procedure utilizing microorganisms which produces a biologically active isomer in combination with synthetic steps which permit the modification of the thus obtained compound However, no purely synthetic method is known which yields a 3,5-trans 6-substituted mevalonolactone which is substantially free of the cis isomer.

Accordingly, there is still a need for a stereospecific method for the synthesis of 5-transubstituted haloalkyl mevalonolactones and derivatives thereof which is simple to practice, proceeds with high yield and results in the trans isomer substantially in the absence of the cis isomer. There is also a need for haloalkyl mevalonolactones and desmethyl derivatives thereof which are useful as intermediates for the preparation of the biologically active derivatives thereof.

SUMMARY OF THE INVENTION

The invention relates to 3-OH, 5-haloalkyl substituted mevalonolactones of the formula

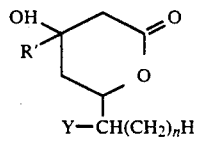

wherein

R' is H or $(CH_3CH_2)_m$, wherein m is 0 to 2;

Y is selected from the group consisting of F, Cl, Br and I; and n is 0 to 12.

In a preferred embodiment of the invention, the above mevalonolactone is the isomer which has the 3-OH and the 5-haloalkyl arranged trans to one another and which is substantially free of the cis isomer.

In a still more preferred embodiment the invention provides a mevalonolactone wherein n is 0 and Y is I and R'=H or $CH_3$.

This invention also relates to a stereospecific method of preparing transubstituted 3-OH, 5-haloalkyl substituted mevalonolactones of the formula

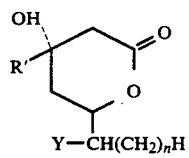

(I)

wherein Y is selected from the group consisting of Cl, Br and $H(CH_2)_nCH=CH-CH_2X$, R' is H or $(CH_3CH_2)_m$, wherein m is 0 to 2, and n is 0 to 12; said method comprising reacting an alkylene halide of the formula

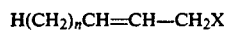

$H(CH_2)_nCH=CH-CH_2X$ with an acylacetic acid ester of the formula

R'COCH$_2$COOR"

wherein R' is H or $(CH_3CH_2)_m$, wherein m is 0 to 2, and R" is selected from the group consisting of $(C_1-C_{30})$ alkyl, $(C_3-C_{30})$cycloalkyl, $(C_6-C_{30})$aryl, $(C_7-C_{30})$ alkylaryl and (C₇-C₃₀)aralkyl, in the presence of an organic ether in a proportion and under conditions effective to form $$MX^-(H(CH_2)_nCH=CHCH_2-CO^-(R')-CH_2COOR'');$$

and
adding thereto Y₂, wherein Y is selected from the group consisting of Cl, Br and I, in a proportion and under conditions effective to form the mevalonolactone of formula (I).

When the mevalonolactone is the one having Y=I and n=0, the alkylene halide has the formula $$CH_2=CHCH_2X$$

This invention further encompasses a method of preparing 3-OH, 5-transubstituted mevalonolactones of the formula (II)

wherein
n is 0-12,
R' is H or (CH₃CH₂)ₘ, wherein m is 0-2, and
Z is selected from the group consisting of and -continued is substituted with H, HO, O, NH₂, RNH, R₂N, OR, R, RCONR, halo, CN, SH, SR, RCOO and fluoroaryl, wherein R is straight or branched alkyl, alkenyl or alkynyl, cycloalkyl, cycloalkenyl, cycloalkynyl, aryl, alkoxy, alkylaryl and aralkyl, and may be further substituted with halo, N, S and O, wherein the dotted lines or circles represent all of the possible oxidation and reduction states of the rings, and p is 0-3; said process comprising obtaining a mevalonolactone of the formula (I)

wherein
R' and n are as defined above; and
Y is selected from the group consisting of Cl, Br and I by the method described above;
reacting said mevalonolactone of formula (I) with a compound of the formula

Z-A wherein
Z is as defined above, and
A is a reactive residue selected from the group consisting of R'''SO, R'''SO₂, R'''₃P and (RO)₂PO, wherein R''' is an aromatic group and R is alkyl or aryl, under reaction conditions effective to form said mevalonolactone of formula (II).

This invention also relates to a method of preparing a compound of the formula (IV)

comprising
obtaining a compound of the formula (I)

wherein
R' is H, Y is I, and n is 0;

converting the compound of formula (I) to an aldehyde of the formula

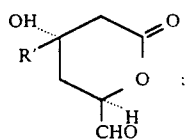
(III)

converting the compound of formula (III) under suitable conditions to an alkene of formula (IV)

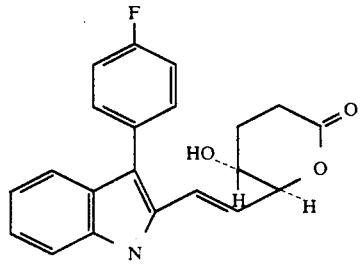
(IV)

which is a known potent hypocholesteremic compound.

Other objects, advantages and features of the present invention will become apparent to those skilled in the art from the following discussion.

DESCRIPTION OF THE PREFERRED EMBODIMENTS

The present invention arose from the desire of the inventors to provide simple one-pot methods for the synthesis of 3-hydroxy, 5-trans-substituted alkyl derivatives of mevalonolactone, some of which are useful as intermediates in the synthesis of hypocholesteremic compounds, and other have hypocholesteremic activities themselves.

In so doing, the inventors also demonstrated that known traditional halolactonization and halocarbonation reactions when applied to the synthesis of the present compounds do not yield transsubstituted mevalonolactone derivatives substantially free of their respective cis isomers in a one-pot reaction from simple, readily available starting materials.

The application of these prior art reactions to the preparation of compounds of the invention is conducted in accordance with the following Schemes.

SCHEME I
HALOLACTONIZATION REACTION

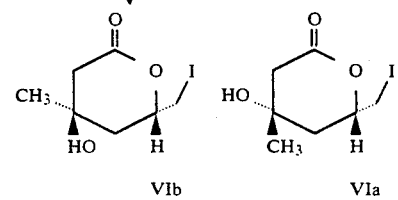

SCHEME II
HALOCARBONATION REACTION

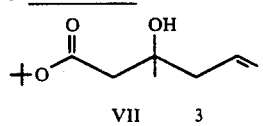

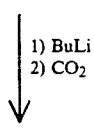

SCHEME II
HALOCARBONATION REACTION

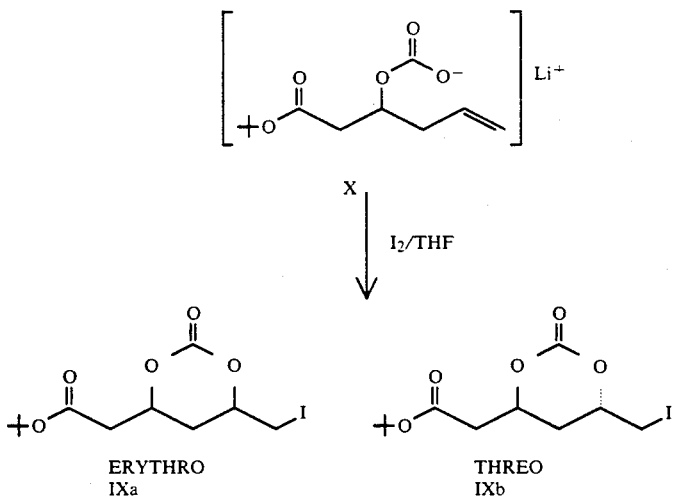

After conducting the prior art halolactonization reaction as described in Scheme I, the mevalonolactone of formula IV was obtained with an overall yield of no more than 20 wt% and a proportion of 80:20 wt.% of the trans:cis isomers.

Similarly, after conducting the prior art halocarbonation reaction described in Scheme II, a mixture of isomers of the structure of IXa and IXb was obtained.

The separation of one isomer from mixtures of the cis and trans isomers requires elaborate purification procedures, sometimes involving chromatographic separation and the like.

Thus, the present method is an unexpected improvement over the prior art methods in that it is capable of producing the 3,5-trans isomer of substituted mevalonolactones in a form which is substantially free of the cis isomer.

The method of the present invention is critically and unobviously different from the previously known iodolactonization procedures, inter alia, in that the cyclization step to obtain the lactone is performed on an ester derivative rather than on a carboxylic acid. Moreover, the carboxylic acid ester derivative is a metal alkoxide ester formed in the first step of the reaction.

The inventive process has the further advantage that it neither requires the isolation nor the purification of any intermediates. Traditional prior art halolactonization reactions require the isolation and purification of the ester of the carboxylic acid derivative, its hydrolysis, isolation and purification of the corresponding carboxylic acid, and finally the iodolactonization of the acid and isolation of the iodolactone.

This invention also relates to a stereospecific method of preparing transubstituted 3-OH, 5-haloalkyl substituted mevalonolactones of the formula

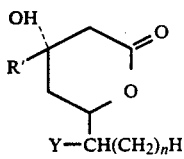

wherein Y is selected from the group consisting of Cl, Br and $H(CH_2)_nCH=CH-CH_2X$, R' is H or $(CH_3CH_2)_m$, wherein m is 0 to 2, and n is 0 to 12; said method comprising reacting an alkylene halide of the formula $$H(CH_2)_nCH=CH-CH_2X$$

with an acylacetic acid ester of the formula $$R'COCH_2COOR''$$

wherein R' is H or $(CH_3CH_2)_m$, wherein m is 0 to 2, and R'' is selected from the group consisting of $(C_1-C_{30})$alkyl, $(C_3-C_{30})$cycloalkyl, $(C_6-C_{30})$aryl, $(C_7-C_{30})$alkylaryl and $(C_7-C_{30})$aralkyl, in the presence of an organic ether in a proportion and under conditions effective to form $$MX^+(H(CH_2)_nCH=CHCH_2-CO^-(R')-CH_2-COOR'');$$

and adding thereto $Y_2$, wherein Y is selected from the group consisting of Cl, Br and I, in a proportion and under conditions effective to form the mevalonolactone of formula (I).

When the mevalonolactone is the one having Y=I and n=0, the alkylene halide has the formula

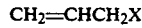

This invention also provides a stereospecific method of preparing transubstituted 3-OH, 5-haloalkyl substituted mevalonolactones of the formula

wherein Y is selected from the group consisting of Cl, Br and $H(CH_2)_nCH=CH-CH_2X$, R' is H or $(CH_3CH_2)_m$, wherein m is 0 to b 2, and n is 0 to 12; said method comprising reacting an alkylene halide of the formula $$H(CH_2)_nCH=CH-CH_2X$$

with an acylacetic acid ester of the formula

R'COCH$_2$COOR"

wherein
R' is H or (CH$_3$CH$_2$)$_m$, wherein m is 0 to 2, and
R" is selected from the group consisting of (C$_1$–C$_{30}$)alkyl, (C$_3$–C$_{30}$)cycloalkyl, (C$_6$–C$_{30}$)aryl, (C$_7$–C$_{30}$)alkylaryl and (C$_7$–C$_{30}$)aralkyl, in the presence of an organic ether in a proportion and under conditions effective to form MX$^+$(H(CH$_2$)$_n$CH=CHCH$_2$—CO$^-$(R')—CH$_2$—COOR");

and
adding thereto Y$_2$, wherein Y is selected from the group consisting of Cl, Br and I, in a proportion and under conditions effective to form the mevalonolactone of formula (I).

When the mevalonolactone is the one having Y=I and n=0, the alkylene halide has the formula

CH$_2$=CHCH$_2$X

The present method relies on the reaction of an alkylene halide with an acyl acetic acid ester and a metal such as Zn or alkali or alkaline earth metals in the presence of an organic ether or other suitably effective solvent, in proportions and under conditions effective to form a halo metal alkoxylate derivative of the carboxylic acid ester, and the addition thereto of an amount of halogen effective to form a mevalonolactone of Formula (I).

The reaction of the alkylene halide with the acyl acetic acid ester can be conducted at a temperature of about −115° to 150° C., Preferably about −20° to 40° C. and more preferably −10° to 25° C. Typically, this reaction is conducted at 0° C. and proceeds at a considerable speed. Although the reaction can be conducted at a pressure of about 5 to 3.8×10$^5$ mmHg, and preferably 550 to 800 mmHg, it is typically conducted at atmospheric pressure.

Examples of suitable alkylene halides are allyl chloride, allyl bromide, 3, 1-bromo-2-butene, 1-chloro-2-pentene, alkylene halides substituted with groups described on page 6, and the like. Examples of suitable organic ethers are ethyl ether, tetrahydrofuran, propyl ether, i-propyl ether, tert-butyl ether, dioxane, dimethoxy ethane, diglyme, and the like. Any organic solvent which does not interfere with the reaction may be utilized. Examples of suitable acylacetic acids are formylacetic acid, acetoacetic acid, propionylacetic acid, butanoylacetic acid, terbutylacetic acid and the like and the esters thereof may be methyl, ethyl, isopropyl, tert-butyl, tert-amyl, cyclopentyl, benzyl, p-methoxybenzyl, methoxymethyl, ethoxymethyl, 1-ethoxyethyl, and the like.

In one embodiment of the process, a mixture of the alkylene halide, the acyl acetate ester, and optionally an organic solvent and/or an organic ether is added to a mixture of the metal and an organic ether or a polar organic solvent. The mixture of the alkylene halide, the ester of the acylacetate and the ether and/or solvent may be added dropwise to the metal and the ether and/or solvent in another particularly preferred embodiment of the method.

The reaction may be allowed to proceed for a period of about 1 to 200 hours, preferably 24 to 48 hours, and typically about 30 to 40 hours, and then the mixture may optionally be cooled prior to conducting the second step in the method.

The halide compound is then added typically at a temperature of about −50° to 25° C., and preferably at a temperature of about −10° to 10° C., at a pressure of about 500 to 800 mmHg, preferably 600 to 760 mmHg, and typically at 0° C. and atmospheric pressure, under which conditions the reaction proceeds at a considerable rate. The reaction may be allowed to proceed for a period of time of about 0.1 to 48 hours, and preferably 2 to 10 hours. Typically the reaction is allowed to continue for 3 to 6 hours.

In a preferred embodiment of the process, the halogen may be added in the form of a solution in an organic solvent. Any organic solvent which does not interfere with the reaction of this step may be employed. Examples of suitable solvents are tetrahydrofuran, dioxane, dimethoxyethane, diglyme and dimethylformamide. However, other solvents may also be utilized within the confines of this invention.

Once the cyclization reaction is concluded, the 3,5-transsubstituted haloalkyl mevalonolactone can be separated from the reaction mixture by methods known in the art.

This compound is typically obtained with an overall yield of about 35 to 48 wt.%. For some of these derivatives, the yield may be has high as 90 wt.%. The content of the cis isomer in these preparations is typically found to be less than 2 wt. % of the trans isomer.

In the present method, the alkylene halide, the acylacetic acid ester and the metal may be present in a proportion of about 1:1:1 to 10:1:10, preferably about 1.1:1:1.5 to 1.2:1:1.3 molar equivalents, and still more preferably with an about 15 wt% excess of alkylene halide and about 20 wt% excess of metal relative to the acylacetic acid ester.

The halogen may be added to the metal alkoxide carboxylic acid ester in a proportion of about 1:1 to 10:1 molar equivalents, preferably about 4:1 to 6:1 molar equivalents.

The reactions of this method may also be conducted utilizing proportions of the reactants outside of those described hereinabove. However, as the content of the reactants strays from the above-stated, side products begin to appear and the yield of the desired product decreases. Nevertheless, for specific purposes it may still be desirable to conduct the reactions outside of the stated reactant's ranges. This is also true for the temperature and the pressure ranges indicated hereinabove. Accordingly, these variables may also be adjusted as suited for a specific purpose.

Any amounts of an organic ether or mixtures thereof may be used in both steps of the process. Preferably, the reactants are present at about 0.01 to 10 molar in the solvent mixture, preferably 0.5 to 2.5 molar, and typically about 1.45 molar. Optionally, a mixture of organic ethers may be utilized. Preferably, a mixture of a less polar ether and a more polar ether, which mixture is present in a proportion of about 20:80 to 80:20 v/v, and more preferably about 40:60 to 60:40 v/v.

In another aspect of the invention there is provided a series of 3-hydroxyl, 5-haloderivatized mevalonolactones of the formula

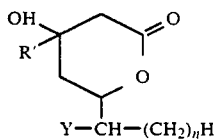

wherein
R' is H or $(CH_3CH_2)_m$, wherein m is 0 to 2;
Y is selected from the group consisting of Cl, Br and I; and
n is 0 to 12.

These are novel compounds which may be prepared by the present method.

In a preferred embodiment of the invention, the above mevalonolactone derivative is a 3-hydroxy1,5-trans isomer substantially free of the cis isomer.

In a still more preferred embodiment the invention provides a mevalonolactone wherein n is O and Y is I and R'=H or $CH_3$.

In still another preferred embodiment of the invention, the mevalonolactone is one wherein Y is I, n is 1, and R' is $(CH_3CH_2)_m$, wherein m is 0 to 1, and more preferably 0. For still another preferred embodiment, R' is H.

Also provided herein is a method of preparing a 3-hydroxyl, 5-trans mevalonolactone of the formula

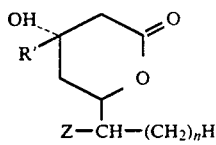

(II)

wherein
R' is H or $(CH_3CH_2)_m$, wherein m is 0-2;
n is 0-12; and
Z is selected from the group consisting of

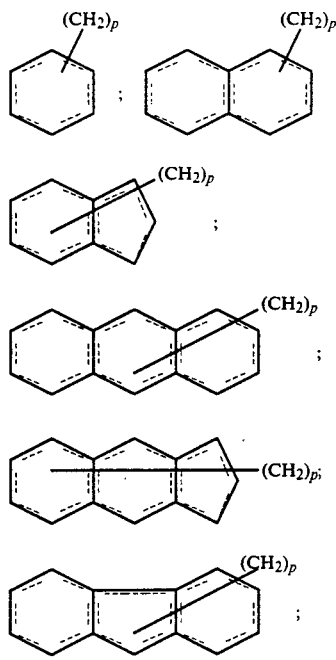

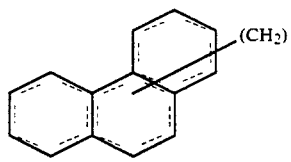

and

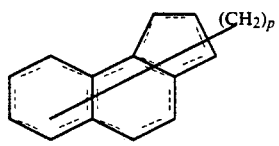

which is substituted with H, HO, O, $NH_2$, RNH, $R_2N$, OR, R, RCONR, halo, CN, SH, SR, RCOO and fluoroaryl, wherein R is straight or branched alkyl, alkenyl or alkynyl, cycloalkyl, cycloalkenyl, cycloalkynyl, aryl, alkoxy, alkylaryl, and aralkyl, and may be further substituted with halo, N, S and O, wherein the dotted lines or circles represent all of the possible oxidation and reduction states of the rings, and p is 0–3, said process comprising obtaining a mevalonolactone of the formula

wherein
R', m and n are as defined above, and
Y is selected from the group consisting of Cl, Br and I, by the method specified above; and
reacting said mevalonolactone of formula (I) either as is or after suitably modifying it to an epoxide or aldehyde as is known in the art, with a compound of the formula Optionally, the OH is protected with a suitable protecting group such as tetrahydropyranyl (THP) as is also known in the art.

Z-A
wherein
Z is as defined above, and
A is a reactive group selected from the group consisting of R'''SO, R'''$SO_2$, R'''$_3$P and $(R_1O)_2PO$, wherein R''' is an aromatic group and $R_1$ is alkyl or aryl, under reaction conditions effective to form said mevalonolactone of formula (II).

The reaction of the mevalonolactone derivative of formula (I) with the various compounds of the formula Z-A is known in the art, as are the conditions under which they should be conducted (e.g., U.S. Pat. No. 4,540,796 to Prugh).

In one preferred embodiment of the hereinabove method the mevalonolactone of formula (I) is reacted with a compound of the formula Z-A, wherein Z is as defined above and A is suitably a reactive group such as R'''SO, R'''$SO_2$, wherein R''', e.g., may be an aromatic residue. This reaction may be conducted as described in U.S. Pat. No. 4,540,796.

A variety of mevalonolactone derivatives having biological activity as hypocholesteremic agents can be prepared by the present method. Examples of such compounds are analogs of compactin, mevinolin (lovastatin), CS-514 and the like.

Also provided herein is a method of preparing a compound of the formula

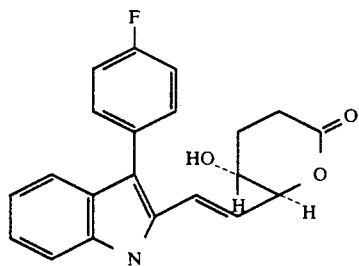

comprising
obtaining a compound of the formula

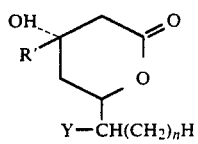

wherein
R' is H, Y is I, and n is 0; converting the compound of formula (I) to an aldehyde of the formula

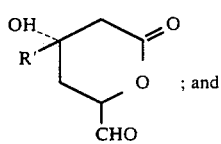

converting the compound of formula (III) under suitable conditions to an alkene of formula (IV)

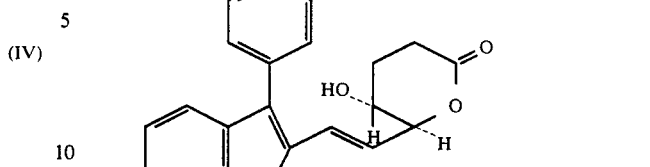

which is a known potent hypocholesteremic compound.

The above methods may be practiced by converting the mevalonolactone of formula (I) to the aldehyde of formula (III) by, e.g., any of the following reactions.

(a) Reacting the mevalonolactone of formula (I) with, e.g., dimethylsulfoxide (DMSO), in the presence of a base such as sodium bicarbonate or triethylamine under known conditions such as temperature and the like. This is exemplified herebelow.

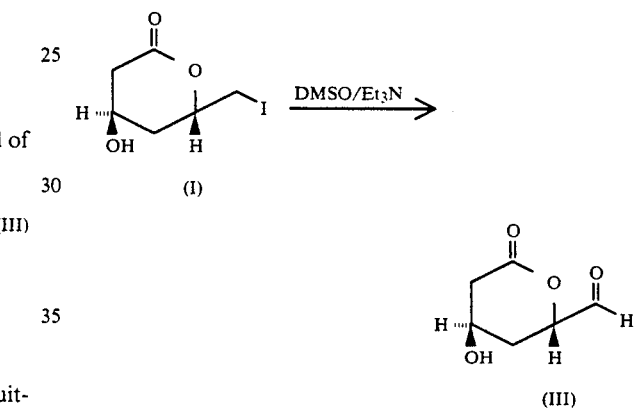

(b) Reacting the mevalonolactone of formula (I) with, e.g., potassium superoxide, and subsequently reducing the intermediate dialkyl peroxide of the formula (Ie) shown below to the corresponding alcohol of formula (If) under standard conditions. The alcohol may then be oxidized by methods known in the art to the aldehyde of formula (III). This is shown below.

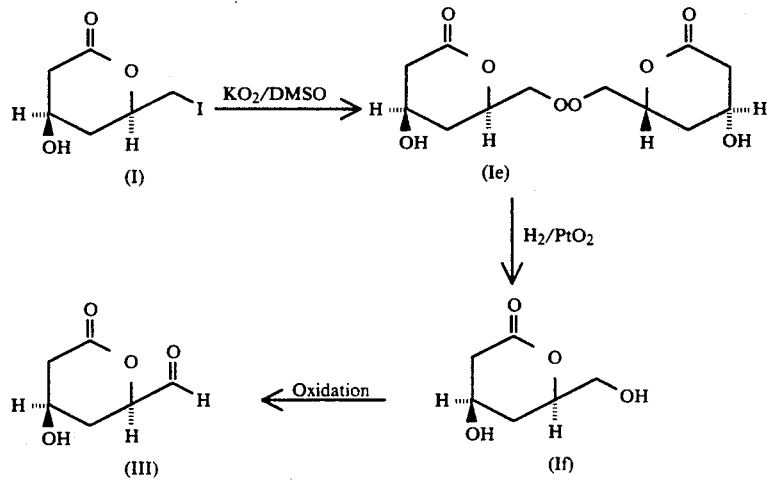

(c) Converting the mevalonolactone of formula (I) to the intermediate phenyl sulfide of formula (Ib), which is then converted to the corresponding sulfoxide of formula (Ic) and further converted to a hemithioacetal not shown The hemithioacetal can then be hydrolyzed to the aldehyde of the formula (III). This step is known as the "Pummerer Reaction" and is shown in Scheme III below.

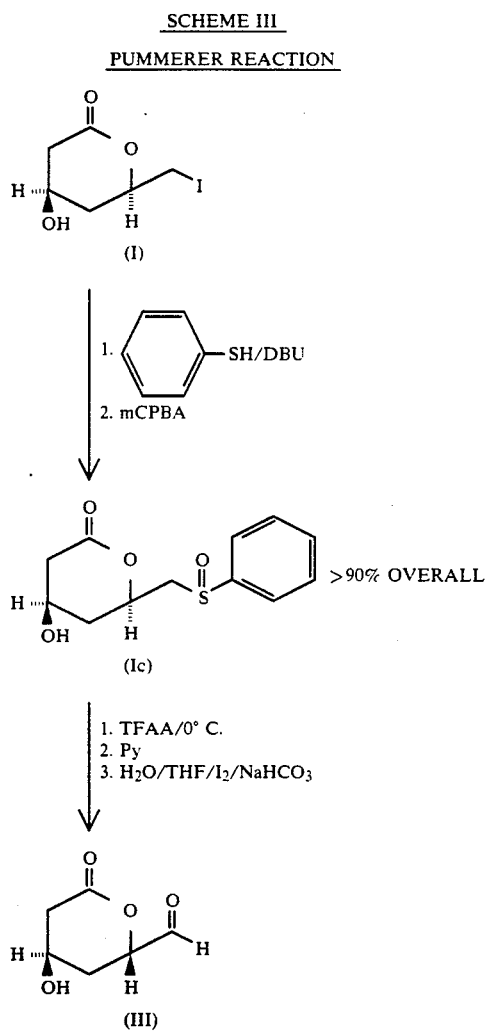

SCHEME III
PUMMERER REACTION

In addition, the preparation of a 3-OH, 5-trans mevalonolactone of the formula (IV) by converting mevalonolactone of formula (I) to that of the aldehyde of formula (III), and then treating the aldehyde of formula (III) with the proper alkyl halide to provide the alkene of formula (IV), may also conducted by methods known in the art.

The compound of formula (IV) may additionally be hydrolyzed by methods known in the art to obtain the compound of formula (V)

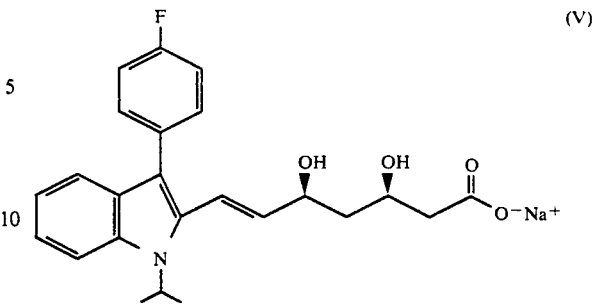

The novel mevalonolactone derivatives of the invention described above are cis and trans mevalonolactones as well as mixtures thereof. The method of the invention provides a selective synthesis for one of these stereoisomers (the trans isomer). The mixture of stereoisomers (cis and trans) may be prepared by methods known in the art.

SCHEME IV
DIASTEREOMERS IN THE OPEN CHAIN AND
LACTONE FORMS OF THE 3,5-DIHYDROXY ACIDS

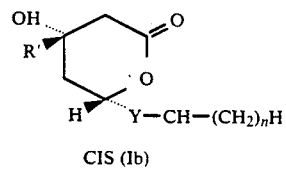

CIS (Ib)

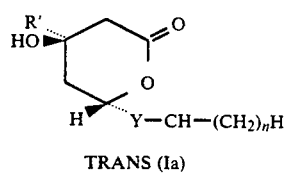

TRANS (Ia)

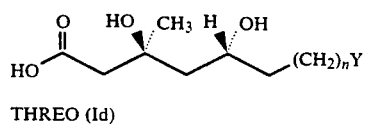

THREO (Id)

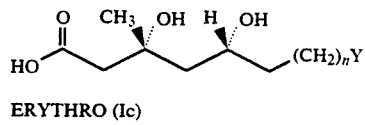

ERYTHRO (Ic)

The mevalonolactones depicted hereinabove may be present in the lactone form (closed ring) or in the open-chain form. The TRANS form of the closed ring mevalonolactone of the formula (Ia) corresponds to the open chain ERYTHRO form of the formula (Ic). Similarly, the closed ring CIS form of the mevalonolactone of formula (Ib) corresponds to the open chain THREO form of the formula (Id).

The presence of a halogen atom in the $C_5$-alkyl substituent of the mevalonolactone of the invention makes it suitable for the preparation of other mevalonolactone derivatives as described in a preferred embodiment of the method of the invention.

Having now generally described the invention, a more complete understanding can be obtained by reference to the examples which are provided herein for purposes of illustration only, and are not intended to be limiting unless otherwise specified.

EXAMPLES

Example 1

Synthesis of 6-iodomethyl mevalonolactone in accordance with the invention.

A mixture of allyl bromide (9.3 mL), tert-butyl acetoacetate (13.6 mL), ether (8 mL), and tetrahydrofuran (THF, 25 mL) is added dropwise to a mixture of granular zinc (7.5 grams) in ether. After disappearance of the zinc, the reaction is stirred for 36 hours and then cooled in an ice bath. A solution of iodine (42 grams) in THF (220 mL) is then added. Six hours later the solution is decolorized by addition of a 10% solution of sodium bisulfite. The organic layer is then separated and washed with brine and dried over magnesium sulfate The aqueous layer is extracted three times with 100 ml of ethyl acetate. Evaporation of the solvent from the organic phase yields a viscous liquid which crystallizes to give pure trans 6-iodomethyl mevalonolactone in a 40-45% yield.

Example 2

Synthesis by Halolactonization Reaction According to Known Method Yielding Mixture of Isomers A mixture of allyl bromide (37 mL) Tert-butyl acetoacetate (54.6 mL), ether (32.5 mL) and tetrahydrofuran (THF, 97.5 mL) is added dropwise to a mixture of granular zinc (30 grams) and ether (66 mL). After the disappearance of the zinc, the reaction is allowed to stir for 36 hours and 4 N sulfuric acid is added until a pH of 2 is obtained. The resulting mixture is saturated with $(NH_4)_2SO_4$ and extracted with $5 \times 100$ mL of ether The combined organic extracts are washed with $2 \times 150$ mL of 1 N aqueous NaOH solution then with $2 \times 150$ mL of saturated brine The solution is dried with $MgSO_4$ then the solvents evaporated to yield tert-butyl 3-hydroxy-3-methyl-5-hexenoate as a light yellow oil. The product may be purified by distillation in vacuo.

To a solution of 13.3 gm of potassium hydroxide in 78 mL of water is added 31 83 gm of tert-butyl 3-hydroxy-3-methyl-5-hexenoate along with sufficient methanol to provide a homogeneous solution. The solution is allowed to stand overnight at room temperature then refluxed for 1 hour. To the solution is added 200 mL of water and solvent is removed at reduced pressure until most of the methanol has been removed. The pH of the solution is then adjusted to 2 by addition of 4 N $H_2SO_4$ and ammonium sulfate is added until a saturated solution is obtained. This solution is extracted with $3 \times 100$ mL of ether. The ether solution is dried with $MgSO_4$ the solvent evaporated to give 16.16 gm (70.5%) of 3-hydroxy-3-methyl-5-hexenoic acid which is distilled at 90°-93° C./0.05 mm Hg.

Following the general procedure of Bartlett (Org. Syn 64:175, 3.25 gm of 3-hydroxy-3-methyl-5-hexenoic acid is dissolved in 80 mL of acetonitrile and cooled to $-2°$ C. To the solution is added 9.1 gm of iodine and the resulting mixture is stored in the dark at 0° C. for 24 hours. The reaction mixture is poured into 50 mL of saturated aqueous sodium bicarbonate and the product extracted with $3 \times 50$ mL of ether. The combined ether extracts are washed with a 10% solution of aqueous sodium thiosulfate until the iodine color is dissipated and then with saturated brine. After drying over $MgSO_4$, the solvent is evaporated to give 2.80 gm (45.5% of theory) of a yellow oil from which 1.26 gm (20.5% of theory) of pale yellow crystals can be isolated. Analysis of the product by proton NMR shows it to be trans-5-iodomethylmevalonolactone that contains an estimated 20% of the cis isomer.

Example 3

Synthesis by Another Known Method Also Yielding Impure Mixture of Isomers.

In an alternate procedure that parallels the iodolactonization that is the subject of this invention, 1.44 gm of 3-hydroxy-3-methyl-5-hexanoic acid are dissolved in 4.2 mL of ether and 4.8 mL of THF and the resulting solution cooled to 0° C. A solution of 5.7 gm of iodine is dissolved in 33 mL of THF and added over the course of 10 min. After 6 hours, the reaction mixture is poured into 60 mL of a 10% aqueous solution of $NaHSO_3$. The phases are separated and the aqueous phase is extracted with $3 \times 50$ mL of ethyl acetate. The combined organic phases are extracted with 50 mL of saturated brine, dried over 2 gm of $MgSO_4$ and the solvent evaporated to give 2.8 gm of a brown solid that NMR analysis shows to be a very impure mixture of cis and trans-5-iodomethylmevalonolactones.

The compound of the formula VI shown in Scheme I above was obtained as a mixture containing about 80 wt% of the trans form (formula VIa) and about 20 wt% of the cis form (formula VIb) with a yield of about 20 wt%.

Example 4

Synthesis by Halocarbonylation Reaction by Known Method.

Tert-butyl 3-hydroxy-3-methyl-5-hexenoate (6 gm) are dissolved in 50 mL of THF and the solution cooled to 0° C. To the cooled solution is added dropwise 13 mL of a 2.5 M solution of n-butyllithium in hexanes. The solution is allowed to warm to room temperature and to remain there for 1 hour after which it is again cooled to 0° C. and a stream of carbon dioxide gas passed through the solution for 20 min. Addition of the $CO_2$ is continued as the solution is warmed to room temperature and held at this temperature for 1.5 hours then cooled to $-75°$ C. The $CO_2$ flow is then terminated and 16.7 gm of iodine dissolved in tetrahydrofuran (THF) added. After 4 hours, the solution is allowed to warm to room temperature over a period of 12 hours and maintained at that temperature for an additional 24 hours. Sufficient 10% aqueous sodium thiosulfate is added to remove the iodine color and then 100 mL of ethyl acetate is added and the phases separated. The aqueous phase is washed with $2 \times 50$ mL of ethyl acetate. The organic phases are combined, decolorized with Norit A then dried over $MgSO_4$. Evaporation of the solvents provides 7.86 gm of an oil. A 3.05 gm aliquot of the oil is subjected to flash chromatography on silica gel to give 1.71 gm (56% of theory) of isolated products. Analysis of the chromatography fractions shows them to contain 0.74 gm of one diastereomer in pure form, 0.22 gm of the other diastereomer in pure form, and 0.75 of an unseparated mixture of the two diastereomers.

Having now fully described the invention, it will be apparent to one of ordinary skill in the art that many changes and modifications can be made thereto, without departing from the spirit or scope of the invention as set forth herein.

We claim:

1. A stereospecific method of preparing a 3-OH, 5-trans mevalonolactone of the formula

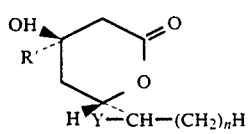

wherein
Y is selected from the group consisting of Cl, Br and I;
R' is $CH_3(CH_2)_m$, wherein m is 0 to 2; and
n is 0 to 12, said method comprising
reacting an alkylene halide of the formula $$H(CH_2)_n-CH=CH-CH_2X$$

wherein X is Cl, Br or I, with an acylacetic acid ester of the formula $$R'COCH_2COOR''$$

wherein R'' is selected from the group consisting of alkyl, cycloalkyl, aryl, alkylaryl and aralkyl, which may be unsubstituted or substituted by alkyl or alkyloxy, and R' is H or $CH_3(CH_2)_m$, wherein m is 0-8, in the presence of an organic ether and a metal M selected from the group consisting of Zn and alkali and alkaline earth metals, in proportions and under conditions effective to form $$MX^+(H(CH_2)_nCH=CHCH_2-CO^-(R')-CH_2COOR'').$$

wherein M, X and R'' are as defined above; and
adding $Y_2$ to said ester wherein Y is selected from the group consisting of Cl, Br and I, in a proportion and under conditions effective to form the mevalonolactone of formula (I).

2. The method of claim 1, wherein
the alkylene halide, the acylacetic acid ester and the metal are present in a proportion of about 1:1:1 to 10:1:10.

3. The method of claim 1, wherein
the $Y_2$ is added in an about three-fold excess with respect to the $ZnX^+(H(CH_2)_nCH=CHCH_2-CO^-(R')-CH_2-COOR'')$.

4. The method of claim 1, wherein
the alkylene halide, the acylacetic acid ester and the metal are reacted at a temperature of about 20° to 40°.

5. The method of claim 1, wherein
the $Y_2$ compound is added to form the mevalonolactone of formula (I) at a temperature of about $-10°$ to 10° C.

6. The method of claim 1, wherein
the $Y_2$ compound is added about 24 hours after the reaction of the acylacetic acid ester with the alkylene halide and the reaction is completed without separating the $MX^{30}$ $(H(CH_2)_nCH=CHCH_2-CO^-(R')-CH_2COOR'')$ from the reaction mixture.

7. The method of claim 1, wherein
the trans isomer of the mevalonate of formula (I) is formed substantially in the absence of the cis isomer.

* * * * *